(12) United States Patent
Levy et al.

(10) Patent No.: US 6,861,211 B2
(45) Date of Patent: Mar. 1, 2005

(54) STABILIZATION OF IMPLANTABLE BIOPROSTHETIC DEVICES

(75) Inventors: Robert J. Levy, Merion Station, PA (US); Narendra Vyavahare, Erial, NJ (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 0 days.

(21) Appl. No.: 09/933,680

(22) Filed: Aug. 22, 2001

(65) Prior Publication Data

US 2002/0081564 A1 Jun. 27, 2002

Related U.S. Application Data

(62) Division of application No. 09/558,709, filed on Apr. 26, 2000, now abandoned.
(60) Provisional application No. 60/131,257, filed on Apr. 27, 1999.

(51) Int. Cl.$^7$ ............................. A01N 1/00; A61F 2/06; A61F 2/08; A61F 2/10; A61F 2/24
(52) U.S. Cl. ..................... 435/1.1; 623/1.1; 623/2.13; 623/13.11; 623/15.12
(58) Field of Search ................... 435/1.1; 600/36; 623/2.13, 1.1, 13.11, 15.12; 8/94.11

(56) References Cited

U.S. PATENT DOCUMENTS

| | | | | |
|---|---|---|---|---|
| 4,378,224 A | * | 3/1983 | Nimi et al. .................. 8/94.11 |
| 4,880,429 A | | 11/1989 | Stone | |
| 4,931,546 A | * | 6/1990 | Tardy et al. ................ 530/356 |
| 5,447,536 A | | 9/1995 | Girardot et al. | |
| 5,660,692 A | * | 8/1997 | Nesburn et al. ....... 204/157.68 |
| 5,782,931 A | | 7/1998 | Yang et al. | |
| 5,865,849 A | * | 2/1999 | Stone .......................... 623/18 |
| 5,891,196 A | * | 4/1999 | Lee et al. .................... 8/94.11 |
| 5,919,472 A | | 7/1999 | Trescony et al. | |
| 6,017,741 A | * | 1/2000 | Keogh ....................... 435/174 |
| 6,166,184 A | * | 12/2000 | Hendriks et al. ........... 530/356 |
| 6,214,054 B1 | * | 4/2001 | Cunanan et al. ......... 623/23.72 |

OTHER PUBLICATIONS

Bernacca et al., "Chemical modification of bovine pericardium and its effect on clacification in the rat subdermal model", Biomaterials 13 (6) : 345–52 (1992).*

* cited by examiner

Primary Examiner—Sandra Saucier
(74) Attorney, Agent, or Firm—Caesar, Rivise, Bernstein, Cohen & Pokotilow, Ltd.

(57) ABSTRACT

The invention relates to methods of stabilizing glycosaminoglycans in a biological tissue (e.g. a bioprosthetic implant) in conjunction with cross-linking of protein in the tissue. The methods of the invention improve the mechanical integrity of the device and improves its stability in vivo. The invention also includes biological tissues having stabilized glycosaminoglycans and cross-linked proteins and kits for preparing such tissues.

20 Claims, No Drawings

STABILIZATION OF IMPLANTABLE BIOPROSTHETIC DEVICES

CROSS-REFERENCE TO RELATED APPLICATIONS

This application is a divisional of application Ser. No. 09/558,709, filed Apr. 26, 2000 now abandoned which is entitled to priority pursuant to 35 U.S.C. §119(e) to U.S. provisional patent application 60/131,257, which was filed on Apr. 27, 1999.

STATEMENT REGARDING FEDERALLY SUPPORTED RESEARCH AND DEVELOPMENT

This research was supported in part by U.S. Government funds (NHLBI grant number HL38118), and the U.S. Government may therefore have certain rights in the invention.

FIELD OF THE INVENTION

The field of the invention is pre-treatment of implantable bioprosthetic devices and tissues.

BACKGROUND OF THE INVENTION

Surgical implantation of biological tissues and prostheses made using biological tissues (collectively, "bioprosthetic devices") is well known and accepted in various medical fields. Examples of well known bioprosthetic devices include heart valves, vascular grafts, skin grafts, Dora mater grafts, pericardium grafts, cartilage grafts and implants, urinary bladder prostheses, ligament prostheses, tendon prostheses, and the like. Other known bioprosthetic devices comprise polymer-encapsulated cells and cell-seeded tissue engineered scaffolds. A significant advantage of valvular bioprosthetic devices, relative to prostheses which do not comprise biological tissue, is that blood coagulation induced by the presence of a prosthesis is usually much lower when a bioprosthetic device is used than when a non-biological prosthesis is used. Also, bioprosthetic devices generally exhibit a reduced incidence of catastrophic failure, relative to non-biological prostheses.

Bioprosthetic devices may be constructed entirely of biological tissue, or they may comprise a combination of biological tissue and synthetic materials. Furthermore, the biological tissue of the prosthesis may be derived from the recipient (usually a human patient), from an animal of the same species as the recipient, from an animal of a species different from the recipient, or from artificially cultured tissues or cells of various origins. Regardless of the source of the biological tissue, a major shortcoming of bioprostheses is that the devices deteriorate over time.

Deterioration of bioprosthetic devices has several manifestations. Implantation of a non-treated biological tissue particularly one derived from an animal of a species different from the recipient) frequently induces an immune response to the tissue in the recipient. Such an immune response causes elements of the recipient's immune system to bind with and destroy the implanted tissue, leading to rapid failure of the device. Even in the absence of an immune response, mechanical stresses exerted upon an implanted tissue (particularly vascular tissues and other implanted tissues which are frequently mechanically stressed) can induce mechanical degradation of the tissue, resulting in thinning or tearing of the tissue or loss of important biological characteristics (e.g. resilience or flexibility). Others have demonstrated that the mechanical and antigenic properties of bioprosthetic devices can be improved by treating the devices prior to implantation with various agents. These pre-implantation treatment methods are generally referred to in the art as "fixation" or "cross-linking."

The most common agent used for fixation of valvular and other collagenous bioprosthetic devices is glutaraldehyde. Other fixative agents which have been used include aldehydes other than glutaraldehyde, various diisocyanates, various polyepoxide ethers, and various carbodiimides as described, for example in U.S. Pat. No. 5,447,536, U.S. Pat. No. 5,782,931, and other U.S. patents which are, as of the filing date of this application, classified in U.S. class/subclass 8/94.11. These prior art fixation methods generally involve treating a bioprosthetic device, prior to implantation, with a chemical agent which, either alone or in combination with another chemical agent, creates a covalent linkage between and within reactive groups of extracellular protein molecules (e.g. amino or carboxyl groups of collagen, elastin, or both). In many fixation methods, this cross-linking step is followed by an additional treatment to retard post-implantation calcification in or on the device.

A shortcoming of prior art bioprosthesis fixation methods is that cross-linking of extracellular proteins in the bioprosthesis inhibits degradation of the bioprosthesis only to a limited degree. Thus, the useful life of the bioprosthesis may be shorter than the remaining life span of the recipient thereof, meaning that the device has to be replaced. It would be tremendously advantageous to extend the useful life of bioprosthetic devices. The present invention provides various methods of extending the useful life of bioprosthetic devices longer than is possible using prior art fixation methods.

BRIEF SUMMARY OF THE INVENTION

The invention relates to a method of treating an implantable biological tissue. The method comprises stabilizing glycosaminoglycans on the tissue and cross-linking proteins on the tissue. The glycosaminoglycans may be endogenous to the tissue or exogenous. In one aspect, the tissue is a part of an implantable bioprosthetic device such as a heart valve prosthesis, a vascular graft, a skin graft, a dura mater graft, a cartilage graft, a cartilage implant, a pericardium graft, a urinary bladder prosthesis, a ligament prosthesis, a tendon prosthesis. For example, the device may be a heart valve prosthesis selected from the group consisting of a porcine heart valve and a bovine pericardium-derived heart valve prosthesis.

In one embodiment of the method of the invention, stabilization of glycosaminoglycans on the tissue is achieved by contacting the tissue with a water-soluble carbodiimide. In this embodiment, cross-liking proteins on the tissue may be achieved by contacting the tissue with a second carbodiimide or with a protein cross-linking agent other than a carbodiimide. Preferably, stabilization of glycosaminoglycans on the tissue is achieved prior to cross-linking proteins on the tissue. Also preferably, the glycosaminoglycan stabilization is performed to the extent that a) the difference between i) the thermal shrinkage temperature of the tissue after contacting the tissue with the carbodiimide and ii) the thermal shrinkage temperature of the tissue prior to contacting the tissue with the carbodiimide is less than half of b) the difference between i) the thermal shrinkage temperature of the tissue after cross-linking proteins on the tissue and ii) the thermal shrinkage temperature of the tissue prior to cross-linking proteins on the tissue.

The water-soluble carbodiimide used in this method may, for example, be 1-ethyl-3-(3-dimethyl aminopropyl) carbodiimide, and the tissue may contacted with the carbodiimide in an aqueous liquid having a pH of about 6.9 to 7.9.

In another embodiment of the method of the invention, stabilization of glycosaminoglycans on the tissue is achieved by contacting the tissue with a carbohydrate oxidizing agent to generate aldehyde groups on the glycosaminoglycans and contacting the tissue with a bi-functional carbohydrate-protein linking agent. The carbohydrate oxidizing agent may, for example, be selected from the group consisting of bromine, periodate, nitric acid, and lead tetraacetate. The bi-functional aldehyde-protein linker may, for example, be selected from the group consisting of glutaraldehyde, a diamine, and an azido hydrazide.

In yet another embodiment of the method of the invention, stabilization of glycosaminoglycans on the tissue is achieved by contacting the tissue with a heterofunctional azide reagent, and optionally by contacting the tissue with an agent for linking the heterofunctional azide reagent and extracellular protein or glycosaminoglycans in the tissue. For example, the agent for linking the heterofunctional azide reagent and extracellular protein in the tissue may be selected from the group consisting of a dithiol, dithiothreitol, a di-aldehyde, glutaraldehyde, a di-carbonyl compound, a carbodiimide, and an epoxide.

The invention also includes a biological tissue treated by the method of the invention.

The invention further relates to a kit for pre-implantation treatment of a biological tissue. This kit comprises a reagent for stabilizing glycosaminoglycans on the tissue and a reagent for cross-ling proteins on the tissue. The kit may further comprise one or more of an instructional material, a container for containing the biological tissue while contacting the tissue with the reagent for stabilizing glycosaminoglycans on the tissue, and a glycosaminoglycan which is exogenous to the tissue.

DETAILED DESCRIPTION

The invention relates to the discovery that stabilization of glycosaminoglycans (GAGs) on a biological tissue improves the durability of the tissue and immune tolerance of the tissue by the recipient. The invention relates to a method of treating an implantable biological tissue such as a tissue of a bioprosthetic device. The method comprises stabilizing glycosaminoglycans on the tissue and cross-linking proteins on the tissue.

The GAGs which are stabilized on the tissue are preferably endogenous to the tissue, but it is recognized that the methods of the invention may also be used to stabilize GAGs which are added to a tissue or to stabilized GAGs which are normally present on the tissue, but which have been modified from their naturally-occurring form.

The methods of the invention are presently intended for stabilization of GAGs on bioprosthetic devices such as heart valve prostheses, vascular grafts, skin grafts, dura mater grafts, pericardium grafts, cartilage grafts or implants, urinary bladder prostheses, ligament prostheses, tendon prostheses, and the like. The biological tissue treated using the methods of the invention may be obtained from the recipient, from an animal of the same species as the recipient, an animal of a different species than the recipient, a tissue culture, or the like.

It is recognized that the methods of the invention can be used to stabilize GAGs on the surface of materials of non-biological origin, wherein the material has surface chemical groups (e.g. carboxyl, sulfhydryl, or amino groups) analogous to groups on the surface of extracellular proteins.

Stabilization of GAGs

The methods of the invention include any known method of stabilizing GAGs on a biological tissue. Preferably, the GAGs are stabilized prior to cross-linking extracellular proteins on the tissue, although protein cross-linking may be performed before GAG stabilization, or simultaneously therewith.

GAGs may be stabilized on a biological tissue, for example, by contacting the tissue with a water-soluble carbodiimide such as a solution of 1-ethyl-3-(3-dimethyl aminopropyl)carbodiimide (EDAC). Unlike protein cross-linking methods involving carbodiimides, it is not necessary to use enhancers of carbodiimide reactivity. That is, GAGs may be stabilized on a biological tissue by contacting the tissue with a water-soluble carbodiimide in the absence of any other chemical compound which reacts with the tissue or the carbodiimide and in the absence of any chemical species which catalyzes the reaction between the carbodiimide and the GAGs on the tissue. Without wishing to be bound by any particular theory of operation, it is believed that the carbodiimide forms a covalent link between a carboxyl group of the GAG and an amino group of an extracellular protein of the tissue.

Carbodiimides have been used by others to attach chemical groups to biological tissues, wherein the chemical groups were not naturally present on the tissue. Carbodiimides have also been used by others to cross-link proteins in a biological tissue in conjunction with secondary cross-linking agents, in conjunction with enhancers of carbodiimide reactivity, or in conjunction with both. Unlike prior art methods, the methods of the invention does not require that the tissue and the carbodiimide be contacted in the presence of any other reactive or catalytic chemical species.

It is understood that, although a limited degree of protein cross-linking may be effected by contacting a biological tissue with a carbodiimide, the degree of cross-linking afforded by such treatment is generally not sufficiently stabilizing that tissue so treated will, following implantation, remain functional longer than tissue which is fixed using accepted methods, such as glutaraldehyde fixation. Thus, it is understood that treating a biological tissue with a carbodiimide alone will increase the thermal shrinkage temperature of the tissue by less than half as much as treatment of the tissue with glutaraldehyde by standard methods (e.g. 0.6% v/v for 24 hours).

It is preferred that the biological tissue and the water-soluble carbodiimide be contacted in an aqueous liquid having a pH near physiological pH (7.4), that is, in a solution having a pH of about 6.9 to 7.9. The duration of the period during which the tissue and the carbodiimide are maintained in contact may vary from about 3 hours to months or more. The period preferably endures for at least about 24 hours. The solution comprising the water-soluble carbodiimide may further comprise one or more of the following: a buffering agent, physiological salts (e.g. NaCl or KCl), a protein cross-linking agent, glutaraldehyde solution, and formaldehyde solution.

Of course, other GAG-stabilizing chemistries can be used in place of carbodiimides. For example, the biological tissue may be contacted with a heterofunctional azide reagent. A heterofunctional azide reagent is a chemical species which has a photoreactive azide moiety and a second chemical moiety which can be linked with a reactive group normally found on an extracellular protein or GAG (e.g. a carboxyl group, a thiol group, or an amine group). The second chemical moiety may be linked chemically with reactive groups on the surface of a bioprosthetic device, and the azide moiety may be photoactivatably linked with molecules on the surface of the device, thereby stabilizing GAG on the surface of the device. The order (if any) in which the azide moiety and the second chemical moiety are linked is not important.

Exemplary heterofunctional azide reagents include amino azides (e.g. 4-{p-azidosalicylamido}butyl amine), thiol azides (e.g. N-[4-{p-azidosalicylamido}butyl]-3'{2'-pyridyldithio}propionamide), activated carboxy azides (e.g. sulfosuccinimidyl 4-{p-azidophenyl}-butyrate and N-succinimidyl-6-{4'-azido-2'-nitrophenylamino}hexanoate), and photo-activatable hydrazides (e.g. sulfosuccinimidyl-4-azidophenyldithiopropionate). Exemplary agents for linking the heterofunctional azide reagent and extracellular protein in the tissue include dithiols (e.g. dithiothreitol), di-aldehydes (e.g. glutaraldehyde), di-carbonyl compounds (e.g. carbodiimides), and epoxides.

Another method of stabilizing GAGs on a biological tissue is to oxidize carbohydrate moieties of the GAGs to generate aldehyde groups and then (or simultaneously) contact the tissue with a bi-functional carbohydrate-protein linking agent comprising a moiety which reacts with the aldehyde groups and another moiety which reacts, either directly, or by way of one or more additional bi-functional linkers, with a chemical moiety (e.g. a carboxyl, sulfhydryl, or amino group) of an extracellular protein of the tissue. According to this method, any of a variety of known carbohydrate oxidizing agents may be used, including, for example, aqueous bromine, dilute nitric acid, aqueous periodate, or lead tetraacetate. Preferably, the oxidizing agent is a periodate. For example, the reaction mixture may comprise 100 millimolar sodium periodate in distilled water at a pH of about 4 to 5, and a biological tissue (e.g. porcine aortic cusps) may be maintained in this reaction mixture for about 24 hours in the dark. The cusps may then be rinsed (e.g. using sterile saline) to remove excess reaction mixture. The bi-functional aldehyde-protein linker used in this method may, for example, be selected from the group consisting of glutaraldehyde, a diamine, and an azido hydrazide.

Stabilization of GAGs on a biological tissue is preferably performed in conjunction with cross-linking of proteins on the tissue. Although the proteins may be cross-linked before the GAGs are stabilized or simultaneously with GAG stabilization, it is preferred that protein cross-linking be performed after GAG stabilization. Substantially any known method for cross-linking proteins in a biological tissue may be used. For example, the cross-linking agent may be glutaraldehyde or another di-aldehyde, a carbodiimide, a polyepoxy ether, or the like. When the GAG stabilizing agent is a carbodiimide, the protein cross-linking agent may be the same or a different carbodiimide. In either instance, carbodiimide cross-linking of proteins requires the presence of either or both of an agent for enhancing the reactivity of the carbodiimide (e.g. N-hydroxysulfosuccinimide) and a second cross-linking reagent for binding an end of the carbodiimide to the extracellular protein of the tissue.

Although the methods of the invention are intended primarily to stabilize endogenous GAGs on a biological tissue, it is understood that these same methods may be used to incorporate exogenous GAGs on the tissue as well. One or more GAGs may be added to the GAG-stabilizing reaction mixture in order to supplement endogenous GAGs or to replace any GAGs which are lost during processing of the tissue. Any of the exogenous GAGs described in the literature may be added to the reaction mixture.

The invention also includes a biological tissue treated by one of the GAG stabilization methods of the invention.

The invention further relates to a kit for pre-implantation treatment of a biological tissue. The kit comprises a reagent for stabilizing GAGs on the tissue and a reagent for cross-linking proteins on the tissue. These reagents are described above. The kit may further comprise one or both of an instructional material which describes GAG stabilization of biological tissues and a container for containing the biological tissue while contacting the tissue with the reagent for stabilizing glycosaminoglycans on the tissue.

The invention is now described with reference to the following Example. This Example is provided for the purpose of illustration only, and the invention should in no way be construed as being limited to this Example, but rather should be construed to encompass any and all variations which become evident as a result of the teaching provided herein.

Definitions

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

An "implantable biological tissue" is a composition of matter comprising living animal cells, extracellular matrix, or both and which may be surgically or topically grafted to the body of a recipient animal such as a human patient. The tissue may be derived from the recipient animal, from an animal of the same species as the recipient, or from an animal of a phylum (e.g. Chordata), sub-phylum (e.g. Vertebrata), class (e.g. Mammalia), genus, or species different from the recipient. Alternately, the tissue may be a manufacture made using cells, extracellular matrix, or both, derived from such animals.

An "implantable bioprosthetic device" is a manufacture which comprises an implantable biological tissue. The device may be the tissue alone, or it may comprise additional elements.

A glycosaminoglycan (GAG) is "stabilized" on a tissue when the tissue is reacted with a reagent which generates at least one covalent bond between the GAG and a molecule of the tissue other than the same GAG.

A protein on a tissue is "cross-linked" when the tissue is reacted with a reagent which generates at least one covalent bond between the protein and another molecule of the tissue (e.g. the same or a different protein or a GAG).

A GAG is "endogenous" to a tissue if the GAG is normally present on the tissue in a healthy individual which naturally comprises the tissue. Otherwise, the GAG is "exogenous" to the tissue.

A carbodiimide is "water-soluble" if it has a greater-than-negligible solubility in water.

EXAMPLE

The experiments presented in this Example demonstrate that the methods of the invention are useful for stabilizing glycosaminoglycans (GAGs) on an implantable biological tissue, and that a GAG-stabilized tissue can also be cross-linked using a known glutaraldehyde-based method.

The materials and methods used in the experiments presented in this Example are now described.

Cross-Linking of Type I Collagen (TIC) and Radiolabeled Hyaluronic Acid (HA)

$^3$H-labeled HA (100 microliters of a 10 milligram per milliliter solution of HA) and TIC (8.06 milliliters of a 3 milligram per milliliter solution of Vitrogen™ 100, Sigma Chemical Co., St. Louis, Mo.; American Radiolabel Co., St. Louis, Mo.) were mixed in a dialysis bag having pores corresponding to a molecular weight cutoff of about 3,500. The dialysis bag was sealed and maintained in 100 milliliters of a first solution which comprised 100 millimolar EDAC and 50 millimolar HEPES at pH 7.4 for 24 hours. Following this treatment, the dialysis bags were maintained in 100 milliliters of a second solution which comprised 0.6% (v/v) glutaraldehyde in HEPES buffer for 24 hours. Separate dialysis bags containing the HA/TIC mixture were maintained in the first solution alone, in the second solution alone, or in neither solution (i.e. in distilled water). Another separate dialysis bag was maintained in 100 milliliters of a solution comprising 100 millimolar ethylene glycol diglycidyl ether (Denacol™ 521, Nagase Chemicals, Ltd., Osaka, Japan).

Following treatment, the HA/TIC mixture was removed from each dialysis bag and rinsed exhaustively with distilled water to remove non-reacted HA until no radioactivity could be detected in the rinse. The remaining material was lyophilized, weighed, and digested in 100 millimolar NaOH prior to determining the radioactivity thereof using standard methods.

Treatment of Porcine Aortic Cusps

Fresh porcine aortic valve cusps were maintained on ice for less than 24 hours between harvesting and the treatment described in this Example. The cusps were rinsed five to six times with cold (4° C.) sterile saline in order to remove blood cells, blood serum, and any other debris which may have been present.

Twenty-five cusps were simultaneously contacted with 100 milliliters of a GAG-stabilizing solution which comprised 50 millimolar HEPES buffer and 100 millimolar 1-ethyl-3-(3-dimethyl aminopropyl)carbodiimide hydrochloride (EDAC) at pH 7.4. The cusps were maintained in this solution at room temperature (i.e. 20° C.) for three to twenty-four hours, and the solution was vigorously agitated during this period in a shaker bath apparatus. Following this treatment, the cusps were rinsed with sterile saline. The rinsed cusps were then maintained in a protein cross-linking solution which comprised 0.2% (v/v) glutaraldehyde and 50 millimolar HEPES buffer, pH 7.4.

Selected cusps were treated with
EDAC and glutaraldehyde;
glutaraldehyde alone;
EDAC alone; or
neither EDAC nor glutaraldehyde.

Following treatment, the thermal shrinkage temperature of the cusps was assessed by differential scanning calorimetry (DSC). Each 5 to 10 milligram tissue sample was hermetically sealed in a DSC aluminum pan. The samples were heated at a rate of 10° C. per minute from 20° C. to 100° C. The peak maxima obtained for denaturation of protein in the cusps were recorded as thermal shrinkage temperature ($T_s$).

The results of the experiments presented in this Example are now described.

Cross-Linking of TIC and HA

By assessing retention of radiolabeled HA on TIC collagen following treatment with various combinations of EDAC, glutaraldehyde, and Denacol™ 521, stabilization of GAGs effected by such treatment was estimated. The relative amounts of radiolabeled HA retained on TIC following various treatments are listed in Table I.

TABLE I

| Treatment | $^3$H-HA Retention ± Standard Error (micrograms $^3$H-HA per milligram TIC) |
|---|---|
| Glutaraldehyde alone | 4.1 ± 0.2 |
| Denacol ™ 521 alone | 5.2 ± 0.2 |
| EDAC + Glutaraldehyde | 14.6 ± 0.3 |

Thus, these results demonstrate that treatment of a TIC/HA mixture with both EDAC and glutaraldehyde results in cross-linking of about three times as much HA to the TIC as treatment with glutaraldehyde or Denacol™ 521 alone.

Thermal Shrinkage Temperature of Treated Porcine Aortic Cusps

The thermal shrinkage temperature of treated cusps was assessed in order to assess cross-linking within the cusp tissue as a measure of mechanical stabilization afforded by the treatment. These results are presented in Table II.

TABLE II

| Treatment | Thermal Shrinkage Temperature (° C. ± 1° C.) |
|---|---|
| neither EDAC nor Glutaraldehyde | 66.3 |
| EDAC alone | 73.2 |
| Glutaraldehyde alone | 87.0 |
| both EDAC and Glutaraldehyde | 86.4 |

These results demonstrate that treating porcine aortic cusps with EDAC alone does not effect as much mechanical stabilization as treatment with EDAC followed by treatment with glutaraldehyde.

The experiments presented in this Example demonstrate that the methods of the invention may be used to stabilize GAGs on a biological tissue prior to implantation of the tissue in a recipient, and that stabilization of GAGs on a biological tissue does not appear to adversely affect mechanical stabilization of the tissue effected by glutaraldehyde cross-linking.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating on implantable biological tissue, said method comprising stabilizing glycosaminoglycans on the tissue and cross-linking proteins on the tissue, wherein the glycosaminoglycans stabilizing comprises contacting the tissue with (a) a water-soluble carbodiimide composition having a pH of 6.9 to 7.9 or (b) a carbohydrate oxidizing agent and a bi-functional carbohydrate-protein linking agent, and the proteins cross-linking comprises contacting the tissue with a cross-linking reagent, wherein the cross linking reagent is a member selected from the group consisting of glutaraldehyde, formaldehyde, a dialdehyde, carbodiimide, and a polyepoxy ether.

2. The method of claim 1, wherein said glycosaminoglycans are endogenous to the tissue.

3. The method of claim 2, wherein the tissue is a part of an implantable bioprosthetic device.

4. The method of claim 3, wherein said device is selected from the group consisting of a heart valve prosthesis, a vascular graft, a skin graft, a dura mater graft, a cartilage graft, a cartilage implant, a pericardium graft, a urinary bladder prosthesis, a ligament prosthesis, and a tendon prosthesis.

5. The method of claim 4, wherein said device is a heart valve prosthesis.

6. The method of claim 5, wherein said heart valve prosthesis is selected from the group consisting of a porcine heart valve and a bovine pericardium-derived heart valve prosthesis.

7. The method of claim 1, wherein the stabilization of glycosaminoglycans on the tissue is achieved prior to cross-linking proteins on the tissue.

8. The method of claim 7, wherein
   a) the difference between i) the thermal shrinkage temperature of the tissue after contacting the tissue with said carbodiimide and ii) the thermal shrinkage temperature of the tissue prior to contacting the tissue with said carbodiimide is less than half of
   b) the difference between i) the thermal shrinkage temperature of the tissue after cross-linking proteins on the tissue and ii) the thermal shrinkage temperature of the tissue prior to cross-linking proteins on the tissue.

9. The method of claim 1, wherein said carbodiimide is 1-ethyl-3-(3-dimethyl aminopropyl) carbodiimide.

10. A biological tissue treated by the method of claim 1.

11. The method of claim 1, wherein the stabilizing of glycosaminoglycans on the tissue is achieved by contacting the tissue with the carbohydrate oxidizing agent to generate aldehyde groups on said glycosaminoglycans and contacting the tissue with a bi-functional carbohydrate-protein linking agent.

12. The method of claim 11, wherein said carbohydrate oxidizing agent is selected from the group consisting of bromine, periodate, nitric acid, and lead tetraacetate.

13. The method of claim 11, wherein the bi-functional carbohydrate-protein linking agent is a member selected from the group consisting of glutaraldehyde, a diamine, and an azido hydrazide.

14. The method of claim 1, wherein the cross-linking comprises contacting the tissue with glutaraldehyde.

15. The method of claim 1, wherein the cross-linking comprises contacting the tissue with glutaraldehyde, provided that the cross-linking is performed after the stabilizing of glycosaminoglycans.

16. The method of claim 1, wherein the stabilizing comprises contacting the tissue with a water-soluble carbodiimide composition having a pH of 6.9 to 7.9, and the cross-linking comprises contacting the tissue with a cross-linking reagent, wherein the cross-linking reagent is a member selected from the group consisting of glutaraldehyde, formaldehyde, a dialdehyde, carbodiimide, and a polyepoxy ether.

17. A method of treating an implantable biological tissue, said method comprising stabilizing glycosaminoglycans on the tissue and cross-linking proteins on the tissue, wherein the glycosaminoglycans stabilizing comprises contacting the tissue with a water-soluble carbodiimide composition having a pH of 6.9 to 7.9, and wherein the cross-linking comprises contacting the tissue with glutaraldehyde.

18. A biological tissue treated by the method of claim 17.

19. A method of treating an implantable biological tissue, said method comprising stabilizing glycosaminoglycans on the tissue and cross-linking proteins on the tissue, wherein the glycosaminoglycans stabilizing comprises (i) contacting the tissue with periodate and (ii) contacting the tissue with a bi-functional carbohydrate-protein linking agent and wherein the cross-linking comprises contacting the tissue with glutaraldehyde.

20. A biological tissue treated by the method of claim 19.

* * * * *